US009957544B2

(12) United States Patent
Steinberg et al.

(10) Patent No.: US 9,957,544 B2
(45) Date of Patent: May 1, 2018

(54) TEST APPARATUS FOR TESTING THE MICROBIAL ACTIVITY ON SURFACES

(71) Applicant: UNIVERSITÄTSKLINIKUM FREIBURG, Freiburg (DE)

(72) Inventors: Thorsten Steinberg, Mannheim (DE); Ali Al-Ahmad, Freiburg (DE); Karen Lienkamp, Gundelfingen (DE); Norbert Nanko, Freiburg (DE)

(73) Assignee: UNIVERSITÄTSKLINIKUM FREIBURG, Freiburg (DE)

( * ) Notice: Subject to any disclaimer, the term of this patent is extended or adjusted under 35 U.S.C. 154(b) by 588 days.

(21) Appl. No.: 14/381,924

(22) PCT Filed: Mar. 1, 2013

(86) PCT No.: PCT/EP2013/000605
§ 371 (c)(1),
(2) Date: Aug. 28, 2014

(87) PCT Pub. No.: WO2013/127536
PCT Pub. Date: Sep. 6, 2013

(65) Prior Publication Data
US 2015/0017680 A1    Jan. 15, 2015

(30) Foreign Application Priority Data

Mar. 2, 2012   (DE) .................. 10 2012 004 028

(51) Int. Cl.
*C12M 1/34*   (2006.01)
*C12Q 1/18*   (2006.01)
(Continued)

(52) U.S. Cl.
CPC ............... *C12Q 1/18* (2013.01); *C12M 25/06* (2013.01); *C12M 33/04* (2013.01); *C12M 41/36* (2013.01); *G01N 1/28* (2013.01); *G01N 30/32* (2013.01)

(58) Field of Classification Search
CPC ................. B01L 1/025; G01N 17/002
See application file for complete search history.

(56) References Cited

U.S. PATENT DOCUMENTS 4,146,433 A    3/1979  Masuda et al.
6,910,445 B1 *  6/2005  Manthei ................. A01K 1/031
                                              119/416

FOREIGN PATENT DOCUMENTS

CN    202 011 880 U    10/2011
DE    197 51 581 A1     4/2000
(Continued)

OTHER PUBLICATIONS

Stansly. "A Bacterial Spray Apparatus Useful in Searching for Antibiotic-producing Microorganisms." Journal of Bacteriology, vol. 54 (Oct. 1947), pp. 443-445.*
Tiller et al., "Polymer Surfaces Derivatized with Poly(Vinyl-N-Hexylpyridinium) Kill Airborne and Waterborne Bacteria". Biotechnology and Bioengineering, vol. 79, No. 4 (Aug. 2002), pp. 465-471.*
Lee et al. "Development of an Aerosol Suface Inoculation Method for Bacillus Spores", Applied and Enviorn. Microbio. vol. 77, No. 5 (Mar. 2011), pp. 1638-1645.*
International search report received in connection with international application No. PCT/EP2013/000605; dated Jun. 4, 2013.

*Primary Examiner* — William H. Beisner
(74) *Attorney, Agent, or Firm* — The Marbury Law Group, PLLC

(57) ABSTRACT

The present invention relates to a device comprising a sample receiving appliance, a receiving appliance for test organisms, preferably for a suspension comprising test organisms, in particular for a bacterial suspension, and a jet pump appliance, wherein the jet pump appliance is, or can be brought, into active connection with the receiving appliance, and wherein the jet pump appliance is designed and installed in order, by means of a propellant medium having a higher pressure than atmospheric pressure at the location of installation of the device to spray test organisms in the (Continued)

form of an aerosol in the direction of the sample receiving installation, wherein the device has an installation for controlling a reproducible pressure of the propellant medium during the spraying of the test organisms and also the use of a device according to the invention.

18 Claims, 1 Drawing Sheet

(51) Int. Cl.
*C12M 1/12* (2006.01)
*C12M 1/26* (2006.01)
*G01N 1/28* (2006.01)
*G01N 30/32* (2006.01)

(56) References Cited

FOREIGN PATENT DOCUMENTS

| | | |
|---|---|---|
| DE | 197 58 598 A1 | 4/2000 |
| DE | 10328556 A1 | 1/2005 |
| DE | 10 2005 038737 A1 | 2/2007 |
| DE | 10 2009046525 A1 | 7/2011 |
| WO | WO 02/085542 A1 | 10/2002 |

* cited by examiner

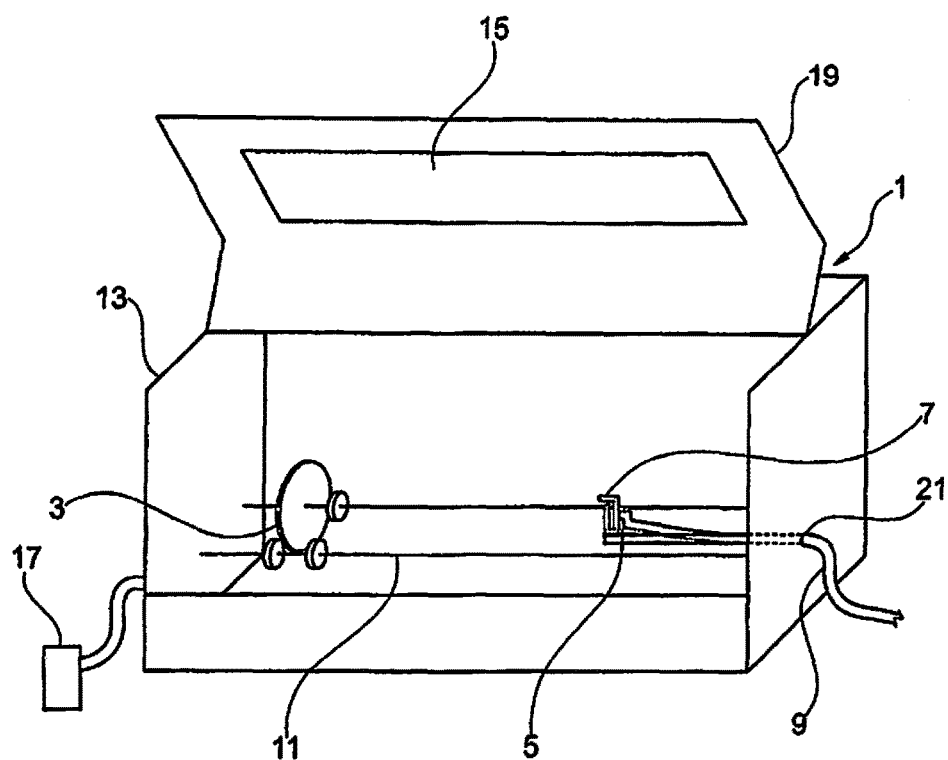

TEST APPARATUS FOR TESTING THE MICROBIAL ACTIVITY ON SURFACES

The present invention directs to a device comprising a sample receiving appliance, a receiving device for test organisms, preferably for a suspension comprising test organisms, in particular for a bacterial suspension, and a jet pump appliance, wherein the jet pump appliance is, or can be brought, into active connection with the receiving appliance, and wherein the jet pump appliance is configured and adapted in order, by means of a propellant medium having a higher pressure than atmospheric pressure at the location of installation of the device, to spray test organisms in the form of an aerosol in the direction of the sample receiving appliance.

Biomaterials are used in medicine for therapeutically or diagnostically purposes. Those can thereby directly contact biological tissue of a body and come in physical, chemical and/or biological reciprocal action with the corresponding biological systems. For example, biomaterials are used in the field of tissue engineering as well as in different fields of medical and dentistry implantology.

For the use of biomaterials those have to fulfill certain requirements. This are the biocompatibility and the biodegradability as well as a preferential treatment of the growth and the differentiation of body's own cells. In contrast to a bacterial contamination of biomaterials forms a great postoperative danger for patients. Such a bacterial contamination is essential to be avoided, if possible.

With biomaterials and as well at other areas of medical engineering, for example with surface coating of medical appliances, as well as with other areas of application, for example with water treatment plants, materials with anti-adhesive respectively anti-microbial surfaces are of advantage.

It is known in the state of the art to get anti-microbial biomaterials by modifications of the surfaces of materials with anti-microbial components, so called "synthetic mimics of antimicrobial peptides".

For verification of the effectiveness of such a treatment of the surfaces of materials are two different testing methods known in the state of the art. With "Aqueous Antibacterial Assays", the surface to be tested is contacted with a bacterial suspension, with "Airborne Antibacterial Assays", bacterial-aerosols are brought into contact with the surface.

With "Aqueous Antibacterial Assays" a test surface is inoculated with a suspension comprising test organisms and covered with a cover glass. The cover glass is than purged with a puffer after a certain contact time and the resulting solution is incubated. In the following the amount of generated bacterial colonies is determined.

A device for a standardized test method for "Aqueous Antibacterial Assays" is known for example from DE 197 51 581 A1. Therein it is disclosed that a sample shall be provided that is incubated with a solution comprising the microorganisms to be tested. Subsequent, the sample shall be transferred into a minimum medium for the respective microorganism and than in a culture medium for the microorganism. Afterwards occurs the taking of the sample and the meteorological survey of the culture medium.

As well DE 197 58 598 A1 discloses a test method for "Aqueous Antibacterial Assays" that shall enable a reproducible measurement of the surfaces.

Disadvantageous of "Aqueous Antibacterial Assays" is that failures may occur within the change over of the bacterias from the cover glass that influence the measurement results. For example, contaminations of the rims of the cover glass with bacterial suspension may occur that have not been in direct contact with the surface to be analyzed. As well, incompletely delimitation of surface adhered cells may occur.

In contrast to is the "Airborne Antibacterial Assay" a simulation of a droplet infection. This is often a more closed to reality contamination of the surface to be analyzed. With the "Airborne Antibacterial Assays" a bacterial suspension is sprayed onto the surface to be analyzed.

DE 10 2005 038 737 A1 discloses a generic device and method for application of test organisms on a surface. Thereby the test organisms are applied by a standard manual sprayer onto the surface to be tested.

Disadvantageous of the generic device for "Airborne Antibacterial Assays" is that no reproducible measurement is possible. Through the use of manual sprayers the spraying volume of the bacterial suspension, the distance of spraying and the pressure of spraying varies.

Furthermore it is problematical that human pathogenic causative organisms are not testable with the generic device. Through the use of manual sprayers there is a risk of a contamination of an area of the laboratory with the human pathogenic causative organisms that has to be avoided.

Therefore it is desirable to be able to revert to a device that enables a standardized testing of material properties with "Airborne Antibacterial Assays".

The object of the present invention is therefore to overcome the disadvantages of the state of the art. In particular, a device shall be provided that allows a reproducible testing of properties of material surfaces with regard to test organisms. Furthermore a device shall be provided that allows a testing of material properties of surfaces with regard to bacterial suspensions, in particular human pathogenic causative organisms.

This objective is solved by the device having an installation for controlling a reproducible pressure of the propellant medium during the spaying of the test organisms.

Through a reproducible pressure of the propellant medium can be ensured that a equal spraying of the test organism onto the surface of a sample to be tested can be provided. A reproducible pressure shall be understood besides other as a constant pressure, a controlled change of pressure, a desired pressure flow during a measurement cycle und/or the like.

This has in particular the advantage that reproducible measurements of the impact of test organisms on the samples is possible so that in particle microbiological testings of surfaces of different samples to be testes are comparable.

By the device according to the invention a standardization of test procedures through controlled test conditions is possible which as well enables a faster and cheaper testing of the samples.

Thereby it may be of advantage that the installation for controlling a reproducible pressure of the propellant medium comprises a valve for regulation of the feeding of the fluid, and wherein preferably compressed air is provided by a compressed air means.

As a propellant medium the use of a gas- and/or vaporous fluid has shown to be in particular of advantage. The use of a liquid propellant medium may in case result in too strong dilution of the sprayed test organisms, in particular of the bacterial suspension.

In particular, the use of compressed air and the use of a compressed air means can be of advantage to provide the propellant. Compressed air and compressed air means are often available and can be used directly.

It can as well be of advantage that a measuring device for measurement of the fed volume of the propellant medium is comprised, in particular a compressed air means comprising a measuring device for measuring the volume of air volume fed.

Such a measuring devices allows a regulation of the propellant medium and a measurement of the volume of the propellant medium fed so that a high reproducibility of the spraying of the test organisms is possible.

According to the invention it is provided that a distance control means for controlling a reproducible distance of the sample receiving appliance from the jet pump appliance is comprised, preferably a rail or the like, in particular comprising a distance measuring device for measuring the distance of the sample receiving appliance from the jet pump appliance.

By a distance control means the distance between the sample receiving appliance from the jet pump appliance can be set reproducibly. The amount of test organisms sprays onto a sample is besides the pressure of the propellant medium and other factors also dependent of the distance from the jet pump appliance from the sample receiving appliance so that a reproducible distance is of advantage for reproducible measurement results.

Thereby it can as well be provided that the sample receiving appliance for test organisms comprises and/or forms an Erlenmeyer flask, preferably comprising an insertion for low volumina of suspension, preferably a tube insertion, in particular a test tub insertion.

The use of an Erlenmeyer flask as receiving device for test organisms is of advantage as with this through the recessed gorge of a Erlenmeyer flask an uncontrolled leakage of liquids is minimized. As well, that can be decontaminated easily.

As well it can provided that the jet pump appliance comprises and/or forms a chromatography spraying attachment.

A chromatography spraying attachment allows an adjusted spraying of the test organisms and can be decontaminated easily.

Thereby it can as well be provided that the sample receiving appliance comprises an attachment device for attaching a material to be analyzed, in particular a substrate holder.

Such a receiving device, in particular a substrate holder, has turned out to be of advantage for a secure fixing of the samples to be analyzed.

Furthermore it can be provided that the receiving appliance in active connection with a magnetic stirrer and/or a heat stirrer, in particular is arranged above a magnetic stirrer and/or a heat stirrer, wherein preferably a magnet, in particular a bar shaped magnet which is in active connection with the magnetic stirrer and/or the heat stirrer, is arranged in the receiving appliance.

By a magnetic stirrer and/or a heat stirrer a good mixing of the test organisms, in particular in a suspension, can be ensured so that advantageously a uniform distribution of the test organisms in the suspension can be achieved.

It can be provided as well that the device comprises a housing, in particular a chamber, preferably a inoculation chamber, wherein at least the sample receiving appliance, the sample receiving appliance for test organisms, the jet pump appliance, the magnetic stirrer and/or the heat stirrer and/or the means for controlling a reproducible distance from the sample receiving appliance and the jet pump appliance is respectively are arranged within the housing, wherein in particular the housing is hermetically sealed.

Thereby it can be provided that the housing forms at least partly a transparent area, wherein in particular the area consists partly of glass and/or plexiglass.

Such a housing enables a user to comply with the good rules of labor work while a spread of aerosols is prevented. Advantageously by the use of such a housing the user can be protected from the used test organisms. By a use of such a housing human pathogens can be used as test organisms as well.

Such a transparent area allows the monitoring of the spraying of the test organism onto the surface to be tested of the sample.

It can be as well of advantage that the housing consists at least partly, in particular completely, of a temperature resistant plastic, in particular polyether ketone (PEEK) and/or aluminium, in particular anodized aluminium.

A housing that consists at least partly of a temperature resistant plastic, in particular polyether ketone (PEEK) and/ or aluminium, can be decontaminated easily. For example such a decontamination is possible within an autoclave. This reduced he amount of time and the costs of a decontamination significantly.

Furthermore it can be of advantage that the housing comprises at least one means for pressure equalization for a, in particular contamination free, pressure equalization between the pressure within the housing and the air pressure at the installation location, in particular a filter for filtering the outlet air, preferably a, in particular autoclavable, teflon filter.

Such a means for pressure equalization is of advantage to avoid that an overpressure occurs in the inner of the housing. By the jet pump raises the volume of fluid inside the housing that is in particular advantageously hermetically closed to avoid a contamination of the user. By the use of a filter a contamination-free pressure equalization from inside the housing with the ambient pressure by the means for pressure equalization can be ensured.

It can as well be provided that the housing comprises an installation for opening an closing, preferably a cover, door and/or the like, wherein the installation consists at least partly of a transparent material.

Such an installation allows an simple insertion and retrieving of the samples, the test organisms, the adjustment of the distance of the sample receiving appliance and receiving appliance for test organisms and/or the like.

Finally it can be provided that the housing comprises a pin for a compressed air means.

Such a pin is of advantage because compressed air is often centrally provided and therefore easy to use.

Furthermore the invention provides a use of a device according to invention for simulation of a transfer of test organisms through airborne infection on a surface, in particular a transfers of bacterias, preferably of human pathogenic microbes, preferably for testing of an anti-microbial activity of a surface.

The present invention is based on the surprising finding that with a device according to the invention a standardized testing of properties of surfaces in view to test organisms can be provided. This can be archived according to the invention that a jet pump for spraying the test organisms, that are in particular present in form of a suspension, is used. For reproducible measurement results the propellant medium of the jet pumpt is fed with a almost constant pressure and a defined distance between the jet pump and a sample receiving appliance can be set and preferably be measured. Thereby can in particular human pathogens be tested as well.

Further features and advantages of the invention result from the following description within embodiments of the invention are illustrated exemplarily by means of schematically drawings without limiting the invention.

BRIEF DESCRIPTION OF THE DRAWING

The FIGURE: a schematic perspective view of a device according to the invention.

The device 1 comprises a sample receiving appliance 3, a receiving appliance for test organisms 5 and a jet pump appliance 7. The receiving appliance 5 is thereby preferably configured for the receiving of suspensions comprising the test organisms. The jet pump appliance 7 is thereby arranged in a way that it is opposite to the sample receiving appliance 3. A compressed air means 9 provides thereby a propellant medium for the jet pumpt appliance 7.

The distance between the jet pumpt appliance and the sample receiving appliance 3 can be set via a distance control means 11. Thereby it is in particular provided that the distance control means comprises a measurement device (not shown) to measure and/or display said distance.

Furthermore, the device 1 comprises a housing 13 having a transparent area 15. In particular the sample receiving appliance 3, the sample receiving appliance for test organisms 5 and the jet pump appliance 7 are in particular arranged within the housing 13. Thereby it can of course be provided that further appliance of the device 1 are arranged within the housing 13 (not shown).

The housing 13 is thereby preferably hermetically lockable so that no test organisms end up in the surrounding area of the housing 13 during spraying of the same with the jet pump appliance 7.

To avoid an overpressure inside the housing 13 a pressure equalization means, in particular a filter or the like, is arranged at the housing 13. By the pressure equalization means a pressure equalization can take place and at the same time in the surrounding area unwanted test organisms can be filtered.

Through a cover 19 an easy access to the inside of the housing 13 can be provided. For feeding the propellant medium is in addition a pin 21 provided, in particular a pin 21 for a compressed air tube.

For a standardized testing of the properties of surfaces in view of test organisms these can at first arranged at the sample receiving appliance 3. These test organisms, in particular provided in form of a suspension, are than inserted into the receiving appliances 5. The jet pump 7 is afterwards brought into active connection with the receiving appliance 5 filled with the suspension. Afterwards, through the distance control means 11 the desired distance between the receiving appliance 5 and the jet pump 7 and the sample receiving appliance 3 is set. To avoid an unwanted distribution of the resulting aerosols during spraying of the suspension the cover 19 is closed. A further observation of the process is possible through the transparent area 15.

By setting the pressure and the feed volume of the propellant medium through the compressed air means 9 a controlled and reproducible application of the sample in the sample receiving appliance 3 can occur. An occurring overpressure inside the chamber 13 is compensated by the pressure equalization means 17.

The features of the present invention disclosed in the description above and in the claims can be used for implementing the invention in its different embodiments both individually and in every possible combination thereof.

LIST OF REFERENCE SIGNS 1 device
3 sample receiving appliance
5 receiving appliance for test organisms
7 jet pump appliance
9 compressed air means
11 distance control means
13 housing
15 area
17 pressure equalization means
19 cover
21 pin

The invention claimed is:

1. A device for reproducible testing of properties of material surfaces with regards to test organisms comprising:
a sample receiving appliance comprising a substrate holder,
a receiving device for test organisms comprising a flask, and
a jet pump appliance,
wherein the jet pump appliance is, or can be brought into, active connection with the receiving device for test organisms comprising a flask, and
wherein the jet pump appliance is configured and adapted in order, by means of a propellant medium having a higher pressure than atmospheric pressure at the location of installation of the device, to spray test organisms in the form of an aerosol in the direction of the sample receiving appliance comprising a substrate holder, characterized in that
the device for the reproducible testing of properties of material surfaces with regards to test organisms has an installation for controlling a reproducible pressure of the propellant medium comprising a valve during the spraying of the test organisms, and wherein the device further comprises:
a distance control means for controlling a reproducible distance of the sample receiving appliance comprising a substrate holder from the jet pump appliance, and optionally comprising a distance measurer for measuring the distance of the sample receiving appliance comprising a substrate holder from the jet pump appliance, and
wherein the receiving device for test organisms comprising a flask is in active connection with a stirrer.

2. The device according to claim 1, characterized in that the installation for controlling a reproducible pressure of the propellant medium during the spraying of the test organisms comprises a valve for regulation of a feeding of the fluid into the appliance.

3. The device according to claim 1, characterized in that the device for reproducible testing of properties of material surfaces with regards to test organisms further comprises a measurer for measurement of the fed volume of the propellant medium.

4. The device according to claim 1, characterized in that the flask is an Erlenmeyer flask.

5. The device according to claim 1, characterized in that the jet pump appliance comprises and/or forms a chromatography sprayer attachment.

6. The device according to claim 1, characterized in that the stirrer is a magnetic stirrer and/or a heat stirrer.

7. The device according to claim 1, characterized in the device for reproducible testing of properties of material surfaces with regards to test organisms comprises a housing, wherein at least the sample receiving appliance, the receiving device for test organisms, the jet pump appliance, and/or the means for controlling a reproducible distance from the sample receiving appliance and the jet pump appliance is respectively are arranged within the housing.

8. The device according to claim 7, characterized in that the housing forms at least partly a transparent area.

9. The device of claim 8, wherein the housing provides for a hermetic seal.

10. The device according to claim 7, characterized in that the housing consists at least partly of a temperature resistant plastic and/or aluminium.

11. The device according to claim 7, characterized in that the housing comprises at least one means for pressure equalization between the pressure within the housing and the air pressure at the installation location.

12. The device according to claim 7, characterized in that the housing comprises an installation for opening and closing, wherein the installation consists at least partly of a transparent material.

13. The device according to claim 7, characterized in that the housing comprises a pin for a compressed air means.

14. The device of claim 7, wherein the housing provides for a hermetic seal.

15. The device of claim 1, wherein the test organisms are human pathogenic microbes.

16. A method for using a device according to claim 1 for simulation of a transfer of test organisms through airborne infection on a surface comprising spraying the test organism in the direction of the sample receiving appliance.

17. The method of claim 16, wherein the test organisms are human pathogenic microbes.

18. The method of claim 16, wherein the method is for testing of an anti-microbial activity of the surface.

* * * * *